(12) United States Patent
Narimatsu (10) Patent No.: US 7,128,715 B2
(45) Date of Patent: Oct. 31, 2006

(54) PRESSURE-PULSE-WAVE DETECTING PROBE OF MANUALLY-OPERABLE TYPE

(75) Inventor: Kiyoyuki Narimatsu, Komaki (JP)

(73) Assignee: Colin Medical Technology Corporation, Komaki (JP)

( * ) Notice: Subject to any disclaimer, the term of this patent is extended or adjusted under 35 U.S.C. 154(b) by 366 days.

(21) Appl. No.: 10/759,013

(22) Filed: Jan. 20, 2004

(65) Prior Publication Data

US 2004/0171946 A1    Sep. 2, 2004

(30) Foreign Application Priority Data

Jan. 21, 2003    (JP)    ............................. 2003-011729

(51) Int. Cl.
*A61B 5/00*    (2006.01)
(52) U.S. Cl. ...................................... 600/503; 600/500
(58) Field of Classification Search .................... None
See application file for complete search history.

(56) References Cited

U.S. PATENT DOCUMENTS 4,469,107 A * 9/1984 Asmar et al. ................ 600/494
6,245,022 B1 * 6/2001 Archibald et al. ........... 600/485
2004/0010199 A1 * 1/2004 Hashimoto et al. ......... 600/502

FOREIGN PATENT DOCUMENTS

JP    A 11-9562    1/1999
JP    A 11-19054    1/1999

\* cited by examiner

*Primary Examiner*—Robert L. Nasser
*Assistant Examiner*—Karen E Toth
(74) *Attorney, Agent, or Firm*—Oliff & Berridge, PLC

(57) ABSTRACT

A pressure-pulse-wave detecting probe for detecting a pressure pulse wave generated by an artery of a living subject, including: (a) a sensor portion which has at least one pressure detecting element and a press surface that is to be positioned manually by an operator, relative to the artery of the subject, and is to be pressed manually by the operator, against the artery of the subject via a body surface of the subject, such that the pressure pulse wave is detected by the above-described at least one pressure detecting element which is arranged on the press surface; and (b) an indicator which is provided to be integral with the sensor portion, and provides an indication as to whether a value of pressure detected by each of the above-described at least one pressure detecting element is suitable for detecting of the pressure pulse wave or not.

5 Claims, 12 Drawing Sheets

PRESSURE-PULSE-WAVE DETECTING PROBE OF MANUALLY-OPERABLE TYPE

BACKGROUND OF THE INVENTION

1. Field of the Invention

This invention relates in general to a pressure-pulse-wave detecting probe including a sensor portion which has a press surface that is to be pressed against an artery of a living subject via a body surface of the subject such that a pressure pulse wave generated by the artery is detected by at least one pressure detecting element arranged on the press surface. More particularly, the invention is concerned with such a pressure-pulse-wave detecting probe of manually-operable type in which a pressing condition of the press surface of the sensor portion is adjustable manually by an operator.

2. Discussion of the Related Art

There is known a pressure-pulse-wave detecting probe including a sensor portion which has a press surface that is to be brought into pressing contact with a predetermined portion of a living subject and pressed against an artery of the subject via a body surface of the subject such that a pressure pulse wave generated by the artery is detected by at least one pressure detecting element arranged on the press surface.

For assuring accurate detection of the pulse wave with use of such a pressure-pulse-wave detecting probe, it is necessary to position the press surface of the sensor portion relative to the artery of the living subject such that the above-described at least one pressure detecting element is positioned right above the artery, and also to force the press surface against the artery with a suitable pressing force. To this end, there is proposed an apparatus for controlling the position of the press surface and the pressing force applied to the artery of the subject. Examples of such an apparatus are disclosed in JP-A-H11-19054 and JP-A-H11-9562 (which are publications of unexamined Japanese Patent Applications laid open 1999).

In each of the apparatuses disclosed in the Japanese publications in which a plurality of pressure detecting elements are provided on the press surface, when the pressure-pulse-wave detecting probe is mounted on a predetermined portion of a living subject, an optimum position of a pressure-pulse wave sensor (i.e.;, the sensor portion) is automatically determined based on a comparison among magnitudes of the pressure pulse waves which are detected by the respective pressure detecting elements. After the determination of the optimum position of the pressure-pulse-wave sensor, the pressing force acting on the pressure-pulse-wave sensor is gradually changed, and an optimum value of the pressing force is automatically determined based on the magnitudes of the pressure pulse waves detected by the pressure detecting elements in process of the gradual change of the pressing force.

In the apparatus disclosed in JP-A-H11-19054, after the optimum position and the optimum pressing force value have been thus determined, the pressing condition is continuously monitored during the detection of the pulse wave. More specifically described, a determination as to whether the optimum pressing force value is maintained is repeatedly made, on the basis of a pressure distribution curve representative of the magnitudes of the pressure pulse waves detected by the respective pressure detecting elements, so that the pressing force is automatically adjusted or changed as needed. In the apparatus disclosed in JP-A-H11-9562, after the determinations of the optimum position and pressing force value, a determination as to whether the optimum position is maintained is repeatedly made on the basis of an amplitude distribution curve representative of amplitudes of the pressure pulse waves detected by the respective pressure detecting elements, so that the position of the pressure-pulse-wave sensor is automatically adjusted or changed as needed.

Each of the above-described apparatuses, arranged to automatically determine the optimum position and pressing force and then maintain them as described above, is capable of accurately detecting the pressure pulse wave. In such an apparatus, however, since the pressure-pulse-wave detecting probe has to be equipped with a moving device for moving the pressure-pulse-wave sensor and also a pressing device for pressing the pressure-pulse-wave sensor, the pressure-pulse-wave detecting probe inevitably has a complicated structure. The probe having the complicated structure, when it is mounted onto a living, subject, requires a somewhat cumbersome operation, and limits a portion of the subject onto which the probe is mountable. Further, the complicated structure of the probe leads to an increase in the cost of manufacture of the apparatus.

Besides the pressure-pulse-wave detecting probe equipped with the moving device and the pressing device, there is known a pressure-pulse-wave detecting probe of manually-operable type, which is to be held, by a hand of operator (e.g. a person who measures the pressure pulse wave) or by a suitable fixture such as a clip and a band, in a predetermined portion of a patient's body during detection of the pulse wave. In operation with such a manually-operable-type probe, the press surface is positioned manually by an operator, relative to the artery of the living subject, and is then pressed manually by the operator, against the artery of the subject via the body surface of the subject. That is, the pressing condition of the press surface of the sensor portion is adjustable manually by the operator. Owing to the absence of the above-described moving and pressing devices, the manually-operable-type probe can be easily mounted onto a living subject, without limiting a portion onto which the probe is mountable.

However, the conventional manually-operable-type pressure-pulse-wave detecting probe has a difficulty in determining the optimum pressing position and pressing force and maintaining them.

SUMMARY OF THE INVENTION

The present invention was made in view of the background prior art discussed above. It is therefore an object of the invention to provide a pressure-pulse-wave detecting probe which is manually operable to suitably adjust the pressing condition and whim is capable of easily and suitably maintaining the pressing position and the pressing force. This object of the invention may be achieved according to any one of the first through eighth aspects of the invention which are described below.

The first aspect of this invention provides a pressure-pulse-wave detecting probe for detecting a pressure pulse wave produced or generated by an arty of a living subject, comprising: (a) a sensor portion which has at least one pressure detecting element and a press surface that is to be positioned manually by an operator, relative to the artery of the subject, and is to be pressed manually by the operator, against the artery of the subject via a body surface of the subject, such that the pressure pulse wave is detected by the above-described at least one pressure detecting element which is arranged on the press surface; and (b) an indicator which is provided to be integral with the sensor portion, and provides an indication as to whether a value of pressure detected by each of the above-described at least one pressure detecting element is suitable for detection of the pressure pulse wave or not.

According to the second aspect of the invention, in the pressure-pulse-wave detecting probe defined in the first aspect of the invention, the indicator provides the indication, by representing whether the detected value of pressure has reached a predetermined threshold or not.

According to the third aspect of the invention, the pressure-pulse-wave detecting probe defined in the first or second aspect of the invention further comprises a handle portion which is provided to be integral with the sensor portion, and which is to be held by the operator during the detection of the pressure pulse wave, so that a position of the press surface relative to the artery and a pressing force applied to the artery can be adjusted manually by the operator, in accordance with the indication provided by the indicator.

According to the fourth aspect of the invention, in the pressure-pulse-wave detecting probe defined in any one of the first through third aspects of the invention, the above-described at least one pressure detecting element consists of a plurality of pressure detecting elements which are arranged in a row on the press surface, wherein the indicator has a plurality of indicating portions one of which indicates whether the value of pressure detected by one of the plurality of pressure detecting elements is suitable for the detection of the pressure pulse wave or not, and another of which indicates whether the value of pressure detected by another of the plurality of pressure detecting elements is suitable for the detection of the pressure pulse wave or not, and wherein the one of the plurality of indicating portions and the above-described another of the plurality of indicating portions are arranged in a direction parallel with the row in which the plurality of pressure detecting elements are arranged According to the fifth aspect of the invention, in the pressure-pulse-wave detecting probe defined in the fourth aspect of the invention, each of the plurality of indication portions of the indicator has a plurality of light emitters each of which emits a light when activated, wherein a number of activated ones of the plurality of light emitters of each of the plurality of indication portions is increased with an increase in the value of pressure detected by a corresponding one of the plurality of pressure detecting elements.

According to the sixth aspect of the invention, in the pressure-pulse-wave detecting probe defined in any one of the first through third aspects of the invention, the above-described at least one pressure detecting element consists of a plurality of pressure detecting elements which are arranged in a plurality of rows on the press surface, wherein the indicator has a plurality of indicating portions which are arranged on a plane parallel to the press surface such that the plurality of indicating portions are positioned in respective positions corresponding to those of the plurality of pressured detecting elements, and wherein each of the plurality of indicating portions indicates whether the value of pressure detected by a corresponding one of the plurality of pressure detecting elements is suitable for the detection of the pressure pulse wave or not.

According to the seventh aspect of the invention, in the pressure-pulse-wave detecting probe defined in the sixth aspect of the invention, each of the plurality of indicating portions emits a light having a color which varies depending upon whether the value of pressure detected by the corresponding one of the plurality of pressure detecting elements is suitable far the detection of the pressure pulse wave or not.

According to the eighth aspect of the invention, in the pressure-pulse-wave detecting probe defined in the sixth or seventh aspect of the invention, the plurality of pressure detecting elements are arranged in a lattice on the press surface, and the plurality of indicating portions are arranged in a lattice on the above-described plane.

In the pressure-pulse-wave detecting probe defined in any one of the first though seventh aspects of the invention, the indicator is provided to be integral with the sensor portion, namely, provided integrally in a body of the pressure-pulse-wave detecting probe. This arrangement permits an operator directly operating the probe, to adjust the pressing condition of the press surface of the probe while observing the indicator which indicates whether the pressure value, detected by each of the above-described at least one pressure detecting element is suitable or the detection of the pressure pulse wave or not. Thus, it is possible to easily establish a suitable pressing condition of the press surface of the probe.

The above-described at least one pressure detecting element arranged on the press surface may consist of a single pressure detecting element. However, it is preferable that the above-described at least one pressure detecting element consists of a plurality of pressure detecting elements arranged in a row on the press surface, as in the pressure-pulse-wave detecting probe defined in the fourth or fifth aspect of the invention. This row arrangement of the plurality of pressure detecting elements, which is conventionally known in the art, facilitates a suitable positioning of the probe relative to the artery of the living subject. That is, by orienting the probe in such a direction that permits the row of the arranged pressure detecting elements to be substantially perpendicular to a direction in which tie artery extends, it is possible to increase an optimum area within which the probe is to be positioned for pressing the artery. Where the plurality of pressure detecting elements are thus arranged in the row, it is preferable that the indicator has a plurality of indicating portions each of which indicates whether the value of pressure detected by a corresponding one of the pressure detecting elements is suitable for the detection of the pressure pulse wave or not, and that the plurality of indicating portions are arranged in the direction parallel with the row of the arranged pressure detecting elements. This arrangement, in which the plurality of indicating portions are positioned in respective positions corresponding to those of the plurality of pressure detecting elements, enables the operator who observes the indicator, to easily know a direction in which the probe is to be displaced, when the position of the probe has to be corrected, The plurality of pressure detecting elements may be two-dimensionally arranged in a plurality of rows or in a lattice on the press surface. The two-dimensional arrangement of the pressure detecting elements makes it possible to further increase an optimum area within which the probe is to be positioned for pressing the artery, thereby further facilitating a suitable positioning of the probe relative to the artery of the living subject. Where the plurality of pressure detecting elements are thus arranged in a two-dimensional manner, it is preferable that the indicator has a plurality of indicating portions which are arranged on a plane parallel to the press surface such that the plurality of indicating portions are positioned in respective positions corresponding to those of the plurality of pressure detecting elements, and that each of the plurality of indicating portions indicates whether the value of pressure detected by a corresponding one of the plurality of pressure detecting elements is suitable for the detection of the pressure pulse wave or not, as in the pressure-pulse-wave detecting probe defined in any one of the sixth through eighth aspects of the invention. This arrangement, in which the plurality of indicating portions are positioned in respective positions corresponding to those of the plurality of pressure detecting elements, enables the operator who observes the indicator, to easily know a direction in which the probe is to be displaced, when the position of the probe has to be corrected. It is noted that each of the plurality of indicating portions may be adapted to emit a light whose color varies depending upon whether the value of pressure detected by the corresponding one of the plurality of pressure detecting elements is suitable for the detection of the pressure pulse wave or not.

BRIEF DESCRIPTION OF THE DRAWINGS

The above and other objects, features, advantages and technical and industrial significance of this invention will be better understood by reading the following detailed description of the presently preferred embodiments of the invention, when considered in connection with the accompanying drawings, in which.

DETAILED DESCRIPTION OF THE PREFERRED EMBODIMENTS

Figure 1:
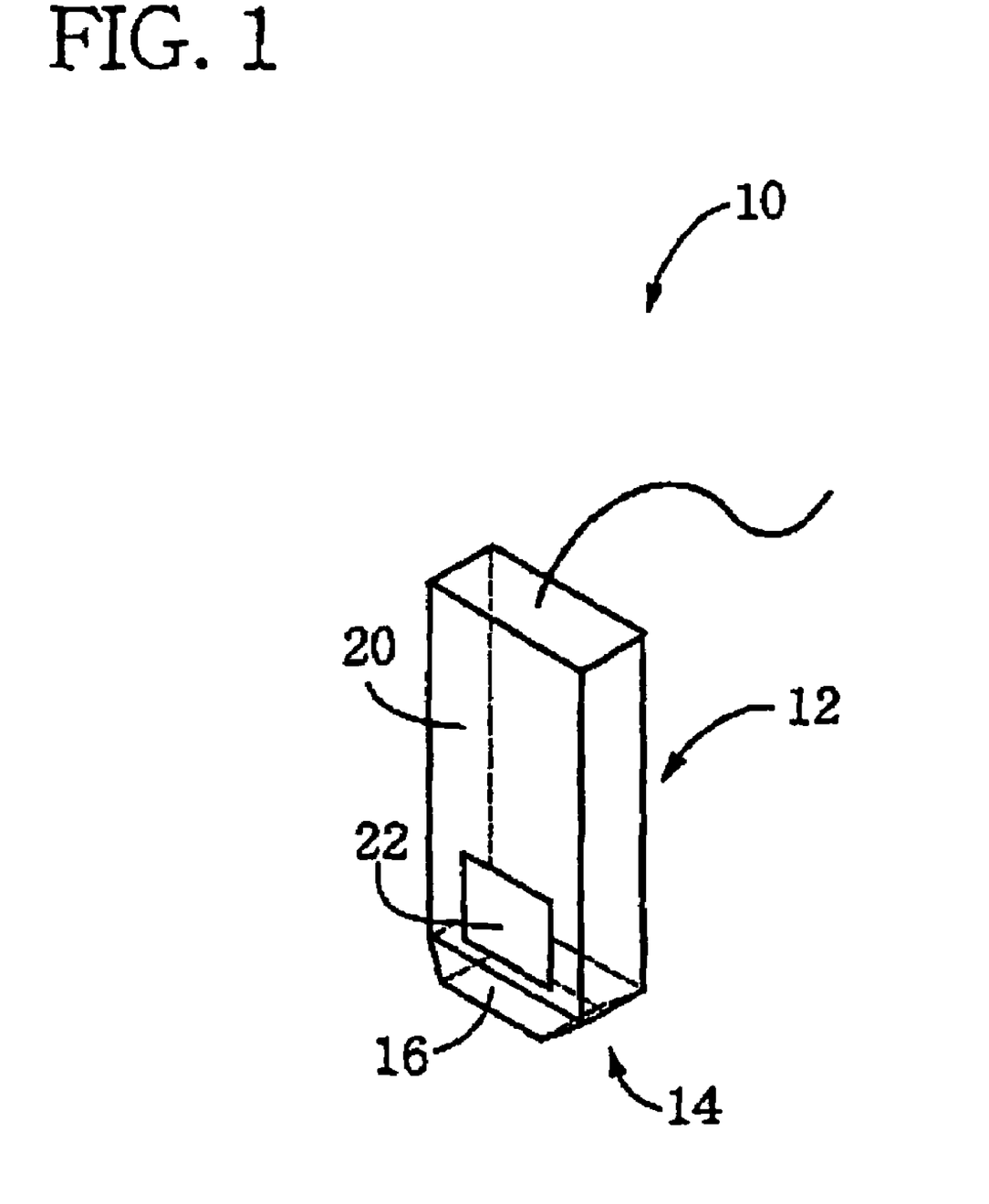
FIG. 1 is a perspective view of a pressure-pulse-wave detecting probe constructed according to a first embodiment of the invention.

FIG. 1 shows a pressure-pulse-wave detecting probe constructed according to a first embodiment of the invention. The probe 10 includes a handle portion 12 which is provided by a generally rectangular parallelepiped body, and a sensor portion 14 which is integrally fixed to a lower surface of the handle portion 12, namely, to one of longitudinally opposite end surfaces of the handle portion 12.

Figure 2:
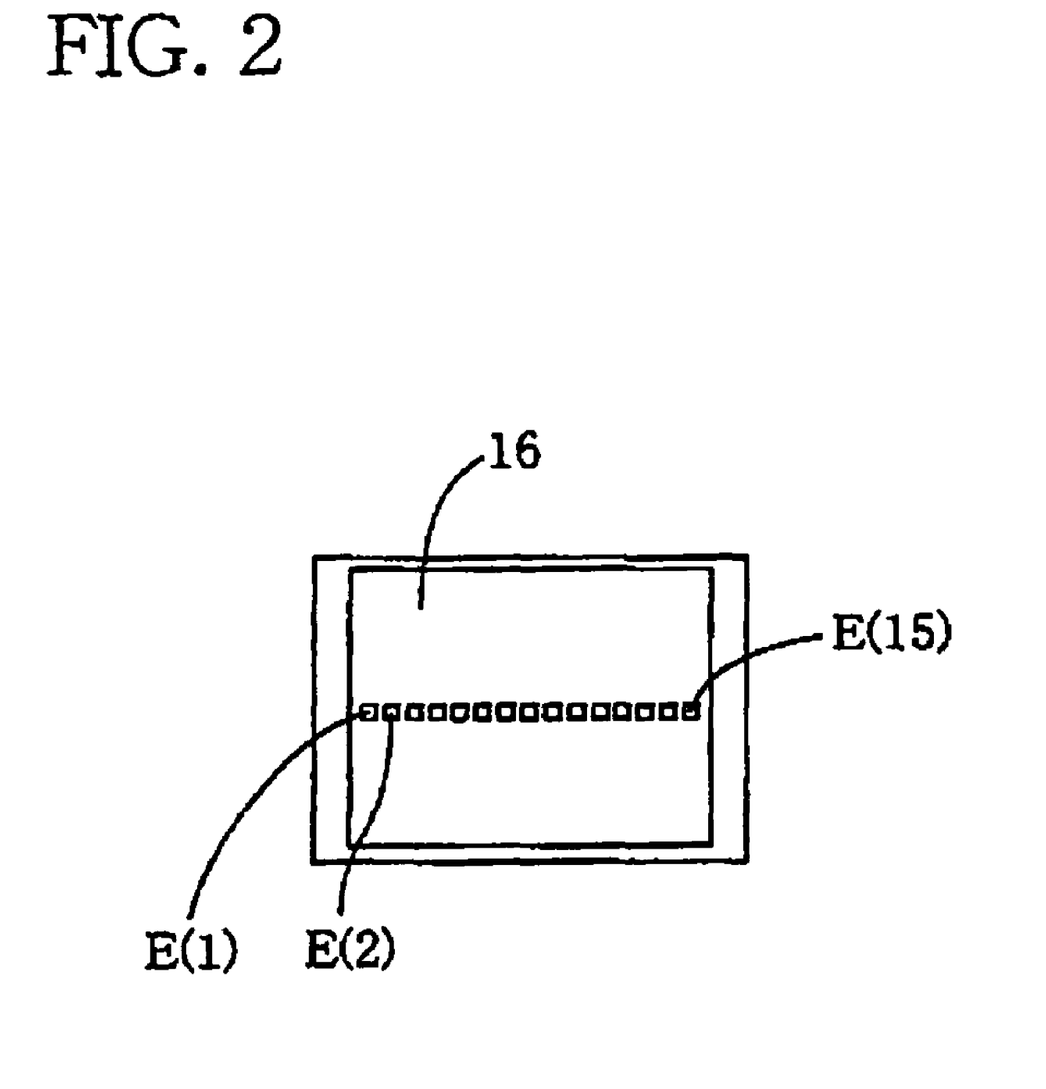
FIG. 2 is a plan view of a press surface of the pressure-pulse-wave detecting probe of FIG. 1.

The sensor portion 14 has a lower surface 16 serving as a press surface which is to be pressed against a skin or body surface of a living subject. This press surface 16 is formed of a semiconductor chip which is constituted principally by a monocrystal silicon. On the press a 16, there are provided a multiplicity of semiconductor sensing elements or pressure detecting elements E which are arranged in a row or array at a constant spacing interval, as shown in FIG. 2. In the present embodiment, the multiplicity of pressure detecting elements E consort of a total of fifteen pressure detecting elements E(1), E(2), . . . , E(15).

Figure 3:
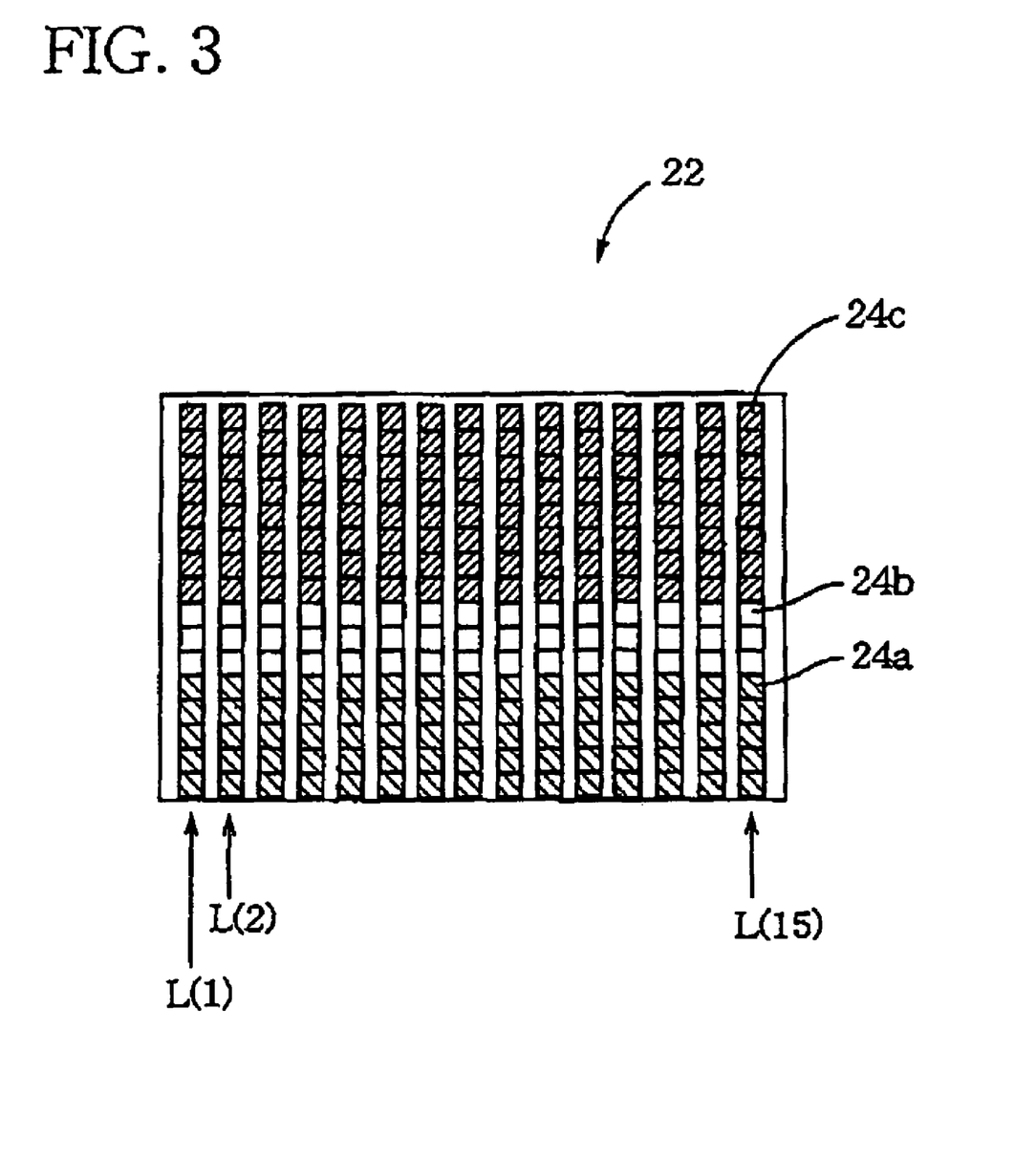
FIG. 3 is a view showing in enlargement an indicator provided in the pressure-pulse-wave detecting probe of FIG. 1.

On a side surface 20 of the handle portion 12 which is parallel with the row of the arranged pressure detecting elements E, there is provided a rectangular indicator 22, as shown in FIG. 1. Since the handle portion 12 is integral with the sensor portion 14 as described above, the indicator 22 provided on the side surface 20 of the handle portion 12 is integral with the sensor portion 14, FIG. 3 is a view showing in enlargement the indicator 22. As shown in FIG. 3, a multiplicity of light emitters in the form of three kinds of light-emitting odes 24a, 24b, 24c which emit lights of different colors when they are activated. In the present embodiment, each of the diodes 24a is adapted to emit a red light, each of the diodes 24b is adapted to emit a yellow light, and each of the diodes 24c is adapted to emit a blue light. The multiplicity of light-emitting diodes 24a, 24b, 24c (hereinafter simply referred to as light emitting diodes 24 when the three kinds of diodes are not particularly distinguished from one another) are arranged in the same number of lines as the number of the above-described pressure detecting elements E, namely, in a total of fifteen lines L(1), L(2), . . . , L(16). Each of the fifteen lines L extends in the vertical direction, i.e., in a direction perpendicular to the row of the arranged pressure detecting elements E. The fifteen lines L are arranged in a direction parallel with the row of the arranged pressure detecting elements E. The light-emitting diodes 24 arranged in each of the lines L cooperate with one another to constitute an indicating portion of the indicator 22. For convenience sake, this term "indicating portion" of the indicator 22 is given the reference sign "L" in the following description.

Each indicating portion L is adapted to indicate whether a value of pressure detected by a corresponding one of the pressure detecting elements E (i.e., one of the elements E given the same number in the parenthesis as that of the line or indicating portion L in question) is suitable for the detection of the pressure pulse wave or not, on the basis of a indication control signal supplied from a arithmetic and control unit 38 which is described later. A number of activated one or ones of the light-emitting diodes 24 of each indicating portion L is increased with an increase in the value of pressure detected by the corresponding pressure detecting element E. Described more specifically, the lowermost one of the light-emitting diodes 24 is first activated, and then the other light-emitting diodes 24 are also activated with the increase in the pressure value detected by the pressure detecting element E, such that a length of a bar constituted by the activated one or ones of the light-emitting diodes 24 represents the detected pressure value. It is therefore possible to know whether the pressure value detected by each pressure detecting element E is suitable for the detection of the pressure pulse wave, by seeing the length of the bar constituted by the activated one or ones of the light-emitting diodes 24. Further, the lowermost one of the light-emitting diodes 24c is adapted to activated to emit the light, when the detected pressure value becomes equal to or higher than a predetermined threshold which corresponds to a minimum value of an optimum range of pressing force. Therefore, an activation of the lowermost one of the light-emitting diodes 24c means that the pressing force acting on the corresponding one of, the pressure detecting elements E is in the optimum range. Where the light-emitting diodes 24a, 24b are activated while none of the light-emitting diodes 24c is activated, it is possible to determine that the pressing force is a little lower than the minimum value of the optimum range. Where only the diodes 24a are activated while none of the diodes 24b, 24c is activated, it is possible to determine that the pressing force is considerably lower than the minimum value.

Figure 4:
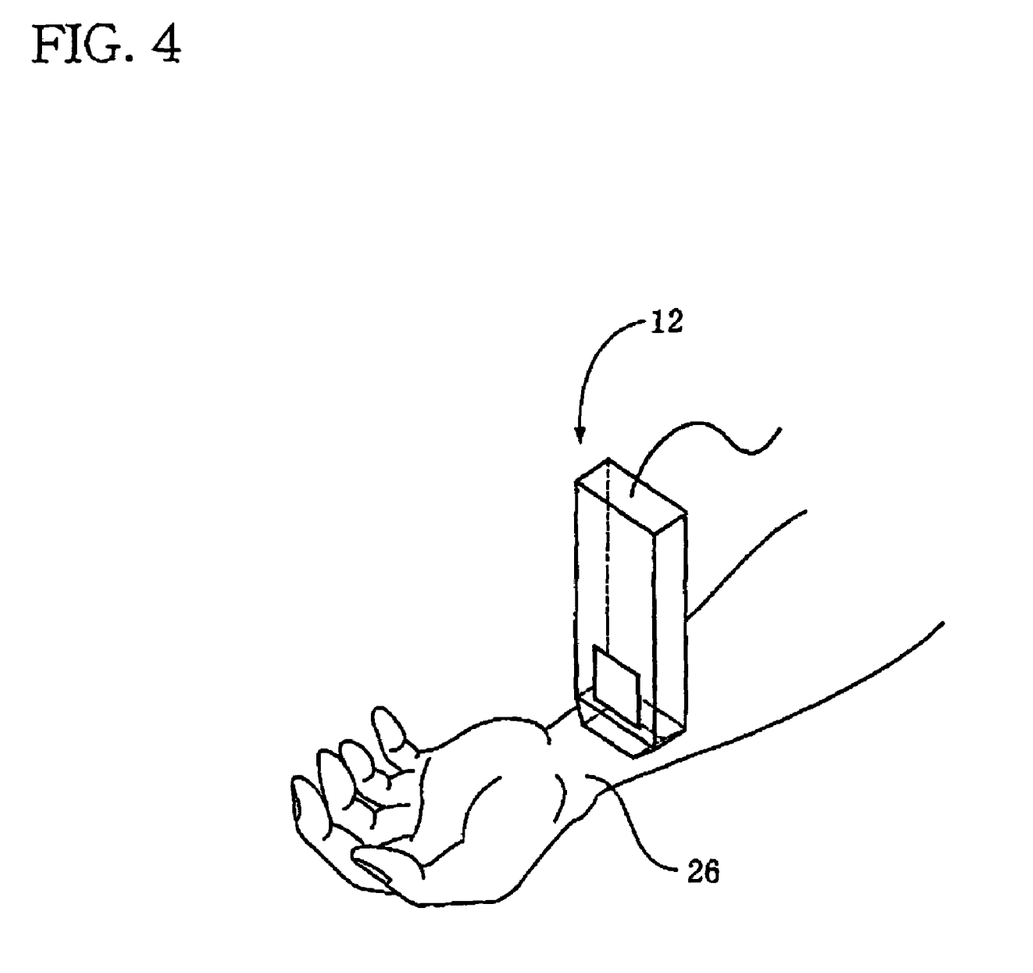
FIG. 4 is a view schematically illustrating the pressure-pulse-wave detecting probe as it is mounted on a wrist of a patience while being held by a hand (not shown) of an operator.

FIG. 4 is a view schematically illustrating the pressure-pulse-wave detecting probe 10 as it is mounted on a writ 26 of a patience while being held by a hand (not shown) of an operator (who measures pressure pulse wave of the patience). Where the probe 10 is mounted on the wrist 26 in which a radius artery extends in substantially parallel with an arm, the probe 10 is oriented, as shown in FIG. 4, in such a direction that permits the row of the arranged pressure detecting elements E (arranged on the press surface 16 of the probe 10) to be substantially perpendicular to the radius artery.

Figure 5:
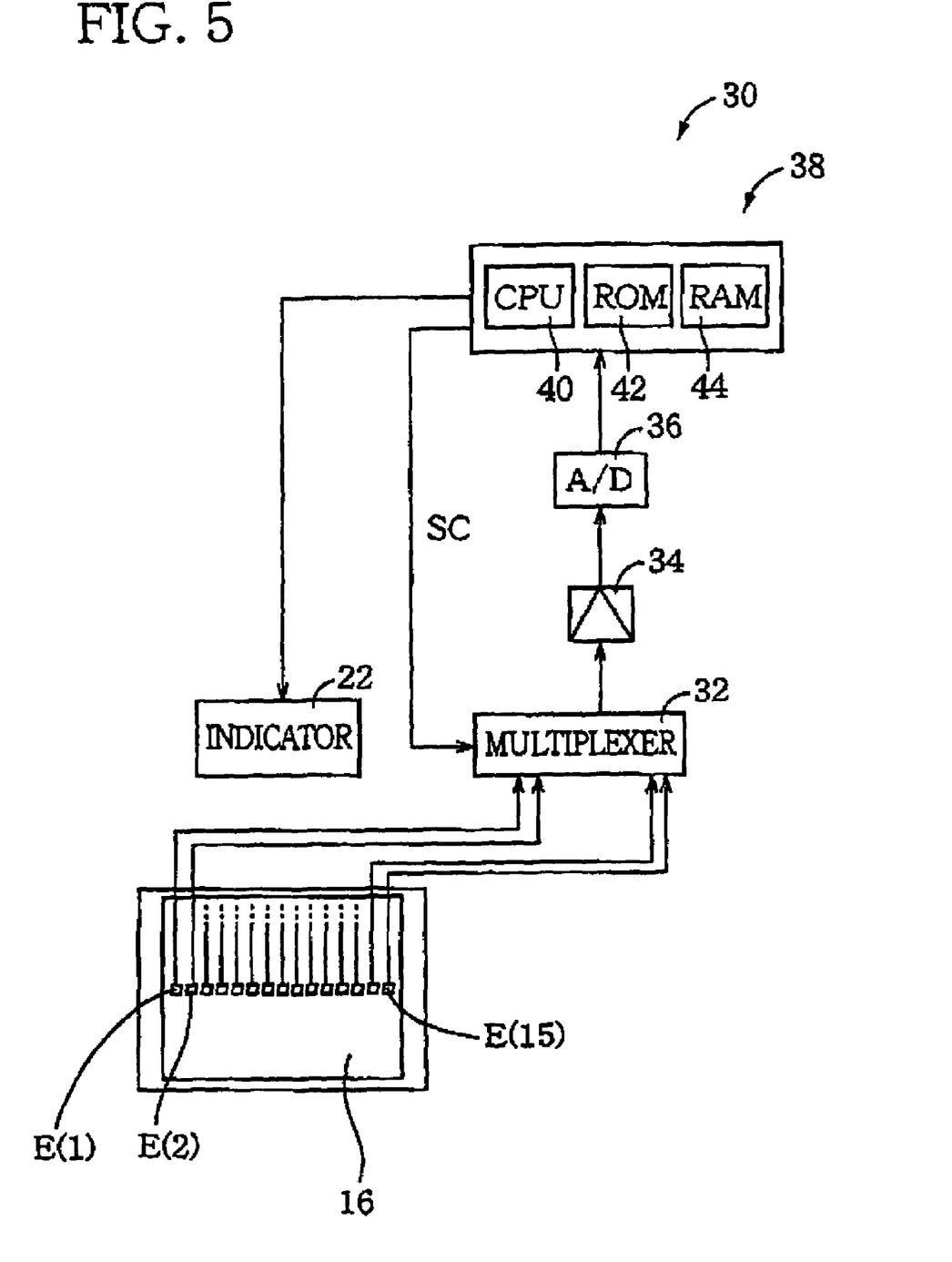
FIG. 5 is a block diagram showing a construction of a pressure-pule-wave detecting apparatus which includes the pressure-pulse-wave detecting probe of FIG. 1.

FIG. 5 is a block diagram showing a construction of a pressure-pulse-wave detecting apparatus 30 which includes the pressure-pulse-wave detecting probe 10. In the apparatus 30, a signal (hereinafter referred to as pressure signal), which is outputted from each of the pressure detecting elements E arranged on the press a 16 and represents the pressure value detected by each of the pressure detecting elements E, is supplied to a multiplexer 32.

In response to a switching signal SC repeatedly supplied from the arithmetic and control unit 38, the pressure signals supplied from the respective pressure detecting elements B are sequentially outputted from the multiplexer 32 to an amplifier 34. In this instance, each of the pressure signals is outputted from the multiplexer 32 for a predetermined length of time which corresponds to a time interval of the repeated supply of the switching signal SC. The pressure signals inputted into the amplifier 34 are then supplied to the control unit 38 via an A/D converter 36.

The control unit 38 is provided by a so-called microcomputer including a CPU (central processing unit) 40, a ROM (read only memory) 42 and a RAM (random access memory) 44, and serves as a indication controller for controlling the indicator 22, such that the pressure value detected by each of the pressure detecting elements E is indicated by the, indicator 22, on the basis of the pressure signal outputted from each of the pressure detecting elements E. The CPU 40 processes signals in accordance with control programs pre-stored in the ROM 42 by utilizing a temporary-storage function of the RAM 44, so as to repeatedly output the switching signal SC at the predetermined time interval and sequentially reads the pressure signals supplied from the respective pressure detecting elements E. Then, the CPU 40 determines, on the basis of the pressure signals, the value of pressure detected by each of the pressure detecting elements E, and supplies the indication control signal to the indicator 22 so that the pressure value is indicated by the indicator 22.

Figure 6:
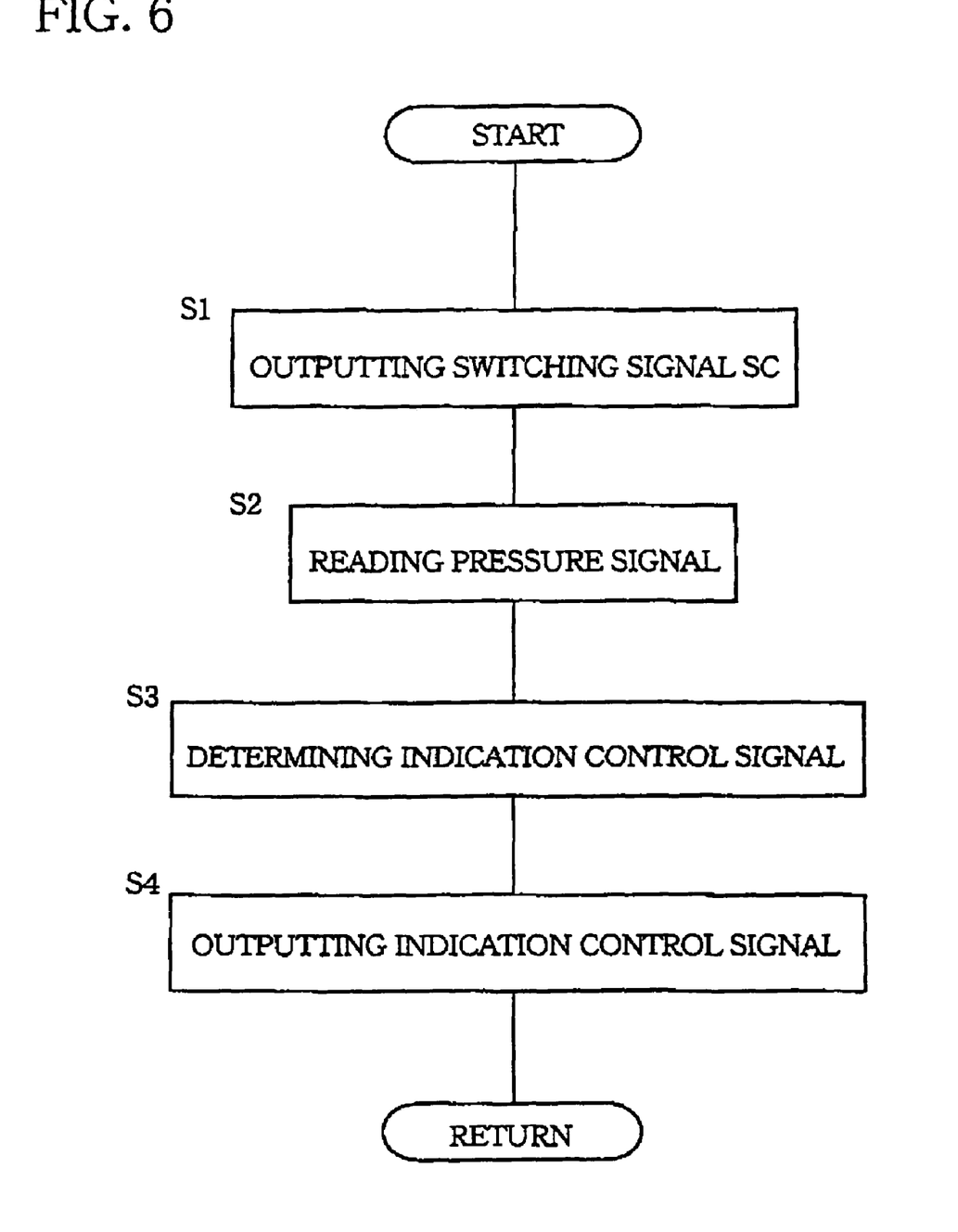
FIG. 6 is a flow chart showing a routine executed by an arithmetic and control unit shown in FIG. 5.

FIG. 6 is a flow chart showing a routine executed by the control unit 38. This routine is initiated with step S1 to output the switching signal SC for switching the multiplexer 32 from one of its operating positions to another of the operating positions. That is, a selected one of the operating positions or channels of the multiplexer 32 is changed to another, in response to the switching signal SC periodically supplied to the multiplexer 32, so that the pressure signals outputted by the respective pressure detecting elements E are sequentially supplied from the multiplexer 32 via the amplifier 34 and the A/D converter 36. Step S1 is followed by step S2 to read the pressure signal currently supplied from the multiplexer 32 via the amplifier 34 and the A/D converter 36.

Step S2 is followed by step S3 to determine the pressure value on the basis of the pressure signal read in step S2, and determine the indication control signal for controlling the indicator 22 such that the determined pressure value is indicated by one of the indicating portions L which corresponds to the pressure detecting element E that has outputted the pressure signal in question. Step S4 is implemented to supply the indication control signal determined in step S3, to the indicator 22. One cycle of execution of the routine of FIG. 6 is terminated with step S4. By repeating the execution of the routine of FIG. 6, the pressure signals outputted by the respective pressure detecting elements E are sequentially read by the control unit 38, and the pressure value indicated by each of the indicating portions L of the indicator 22 is successively updated.

Figure 7:
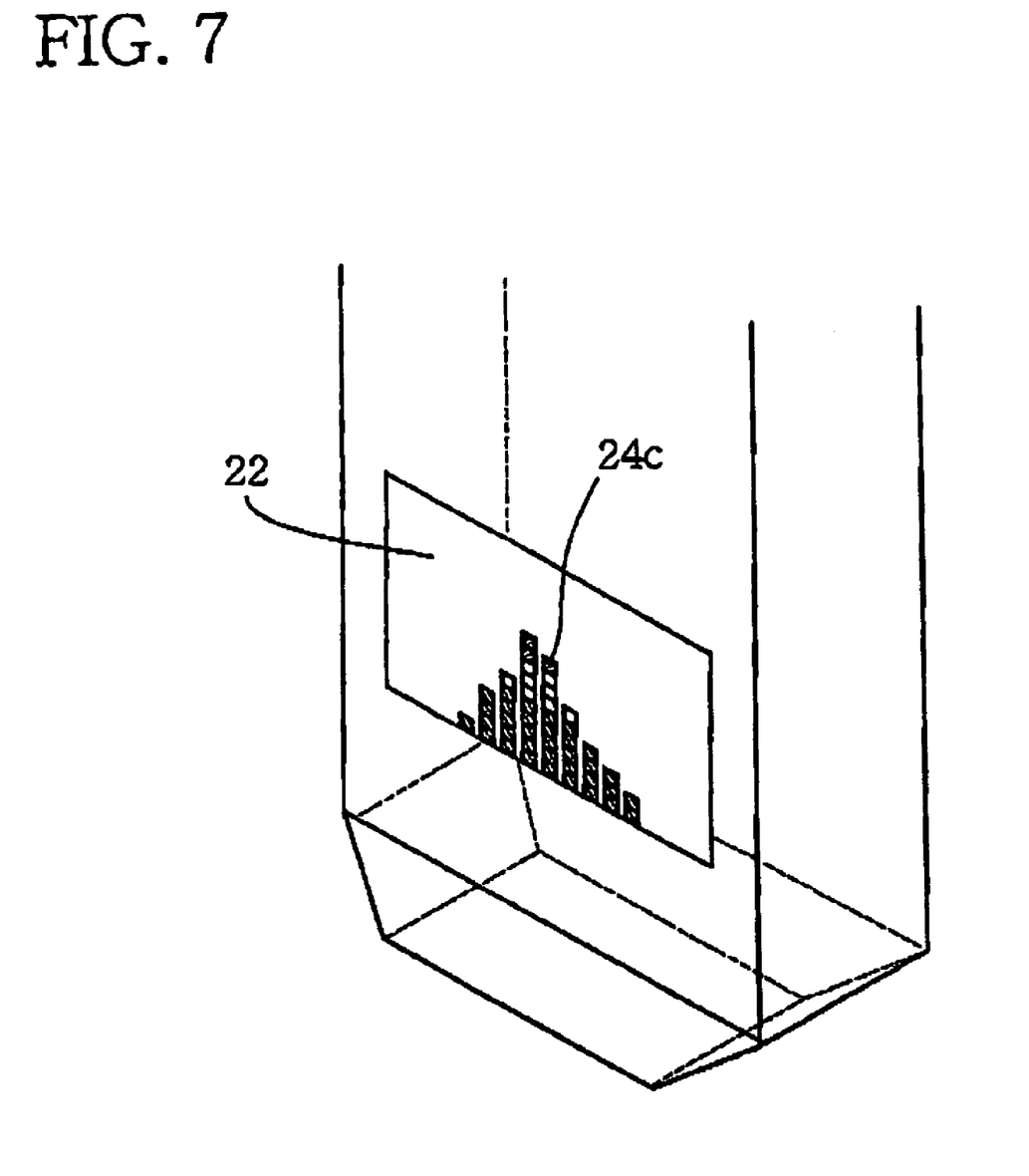
FIG. 7 is a view of an example of indication provided by the indicator in execution of the routine shown in FIG. 6, wherein the indicator indicates that the press sure of the probe is in a suitable pressing condition.
Figure 8:
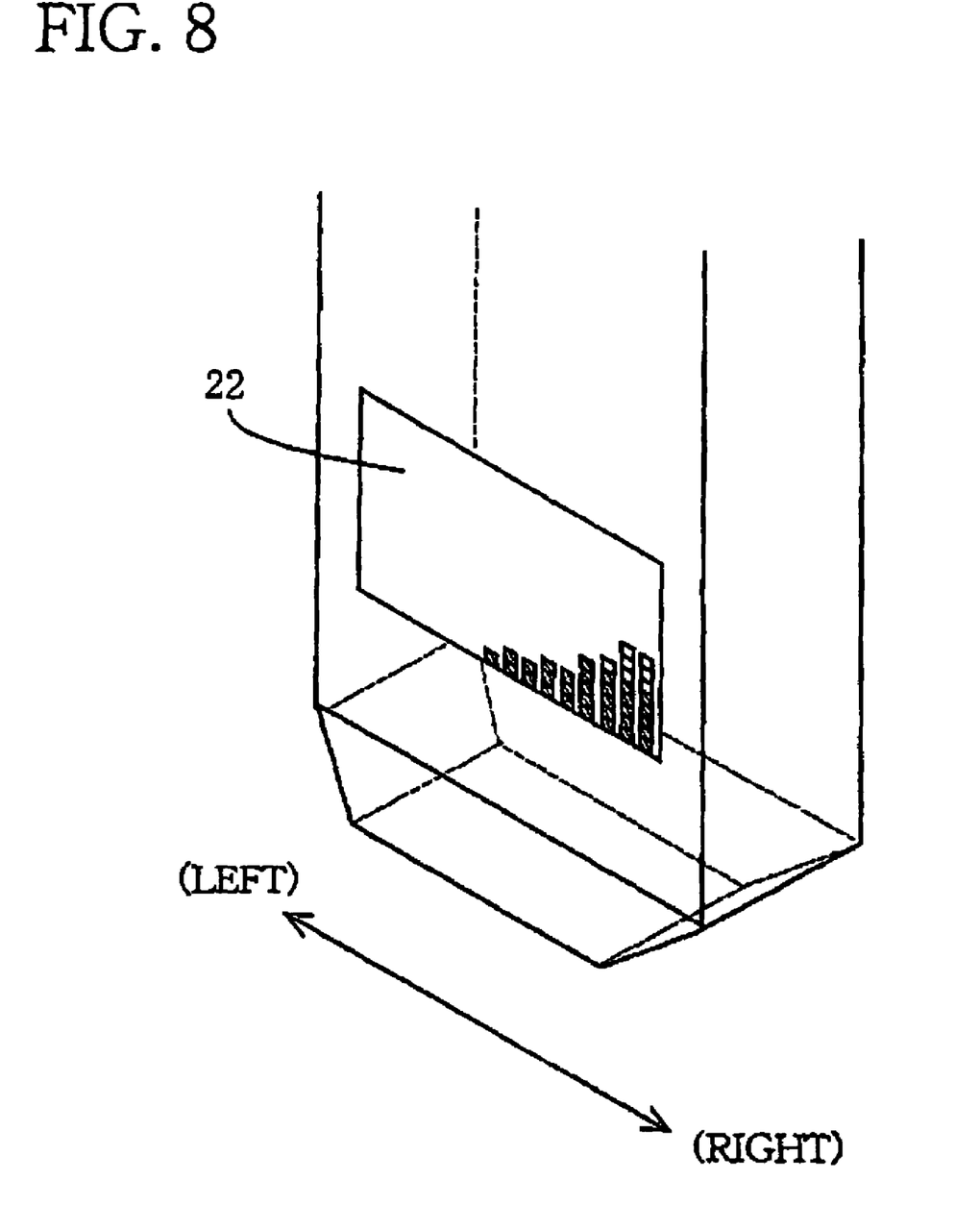
FIG. 8 is a view of another example of indication provided by the indicator in execution of the routine shown in FIG. 6, wherein the indicator indicates that the press surface of the probe is not in a suitable pressing condition.

FIG. 7 is a view of an example of indication provided by the indicator 22 in execution of the routine of FIG. 6. In the example of FIG. 7, the highest one of the pressure values is indicated by one of the lines or indicating portions L which is located at substantially the middle of the array of the indicating portions L. This indicates that the pressure value detected by one of the pressure detecting element E which is at substantially the middle of the array of the elements E is the highest among the pressure values detected by the respective elements E, and that the pressure-pulse-wave detecting probe 10 is positioned in a suitable position relative to the artery of the living subject. Further, in this example of FIG. 7, since the light-emitting diodes 24c (at least the lowermost one of which is activated when the detected pressure value is not lower than the minimum value of the optimum range of pressing force) are activated to emit the lights, it is possible to determine that the pressing force is in the optimum range. On the other hand, in another example shown in FIG. 8, the pressure value indicated by each indicating portion L is increased as viewed in the rightward direction as seen in FIG. 8. This indicates that the pressure-pulse-wave detecting probe 10 is not positioned in the suitable position.

Further, as described above, the direction of the array of the indicating portions L is parallel with that of the array of the pressure detecting elements E. The position of each of the pressure detecting elements E in the array corresponds to the position of a corresponding one of the indicating portions L in the indicator 22, which one indicates whether the pressure value detected by the detecting element E in question is suitable for the detection of the pressure pulse wave. Therefore, in case of the example of FIG. 8 in which relatively high pressure values are indicated by ones of the indicating portions L which are located in the right end portion of the array of the indicating portions L, it is possible to know that relatively high pressure values are detected by ones of the pressure detecting elements E which are located in the right end portion of the array of the elements E. The pressure-pulse-wave detecting probe 10 can be positioned in the suitable position, simply by moving the probe 10 in the rightward direction, i.e., in a direction in which the pressure value indicated by each indicating portion L is increased.

As described above, in the pressure-pulse-wave detecting probe 10 constructed according to the present embodiment of the invention, the indicator 22 is provided to be integral with the sensor portion 14, namely, provided integrally in a body of the pressure-pulse-wave detecting probe 10. This arrangement permits an operator holding the probe 10 to adjust the pressing condition of the probe 10 while observing the indicator 22 which indicates whether the pressure value detected by each of the pressure detecting elements E is suitable for the detection of the pressure pulse wave or not. Thus, it is possible to easily establish a suitable pressing condition of the probe 10.

Further, in the probe 10 of the present invention in which the plurality of pressure detecting elements E are arranged in the single row on the press surface 16 of the sensor portion 14, the position of each of the indicating portions L in the indicator 22 corresponds to the position of a corresponding one of the pressure detecting elements E in the array of the elements E, which one detects the pressure whose value is indicated by the indicating portion L in question This arrangement enables the operator who observes the indicator 22, to easily know a direction in which the probe 10 is to be displaced, when the position of the probe 10 has to be corrected Referring to FIGS. 9–12, there will be described a second embodiment of this invention, wherein the same reference sign as used in the above described first embodiment will be used to identify the functionally corresponding elements.

Figure 9:
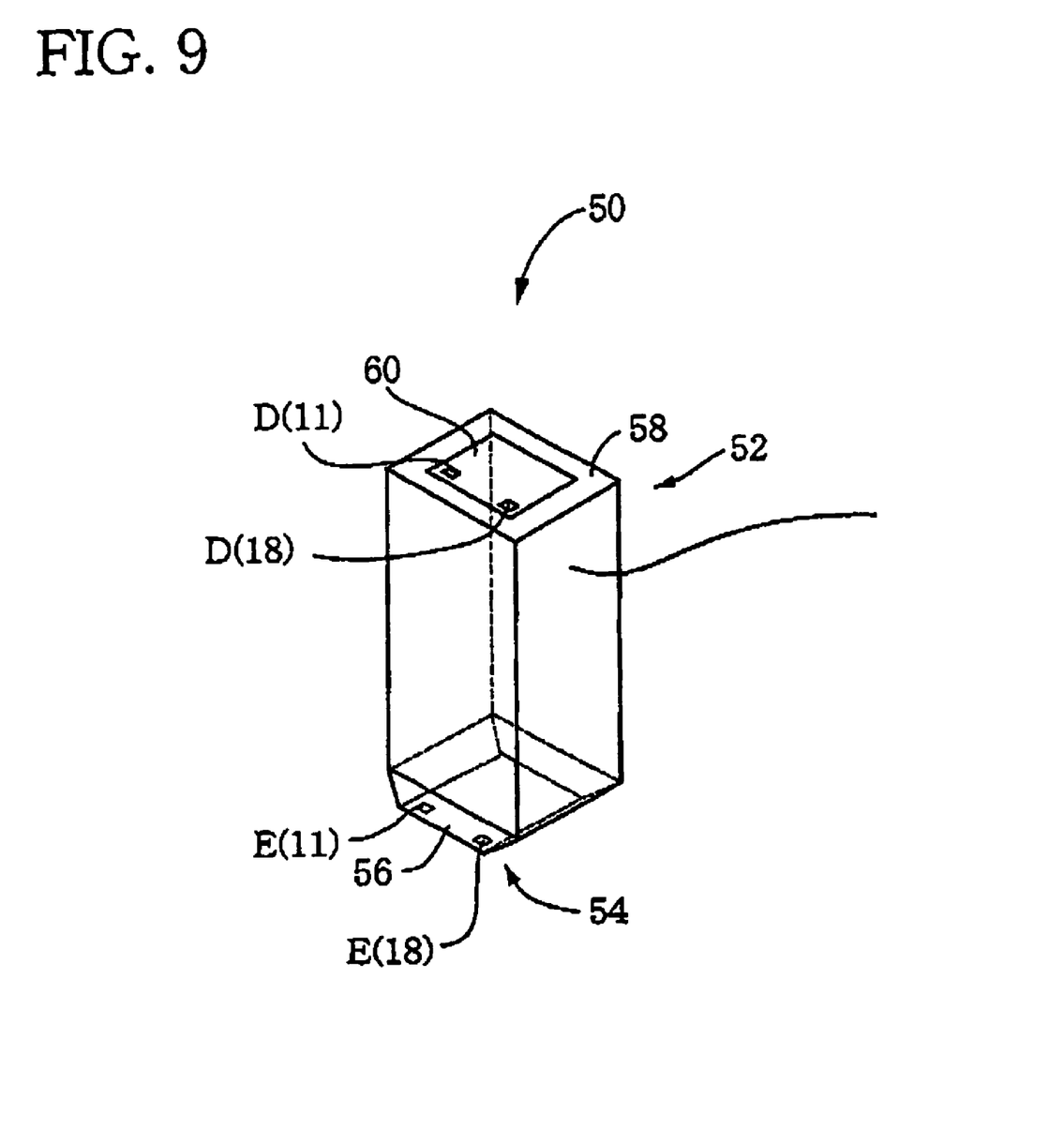
FIG. 9 is a perspective view of a pressure-pulse-wave detecting probe constructed according to second embodiment of the invention.

FIG. 9 is a perspective view of a pressure-pulse-wave detecting probe 50 constructed according to the second embodiment of the invention The probe 50 includes a handle portion 52 and a sensor portion 54 which is integrally fixed to a lower surface of the handle portion 52, namely, to one of longitudinally opposite end surfaces of the handle portion 52. This probe 50 is different from the probe 10 of the above-described first embodiment, in that the handle portion 52 has in its transverse cross section a generally square shape rather than a rectangular shape, and in that an indicator 60 is provided in an upper surface 58 of the handle portion 52 that is parallel with a press surface 56 of the sensor portion 54. In the second embodiment, the upper surface 58 of the handle portion 52 corresponds to a plane parallel to the press surface 56.

Figure 10:
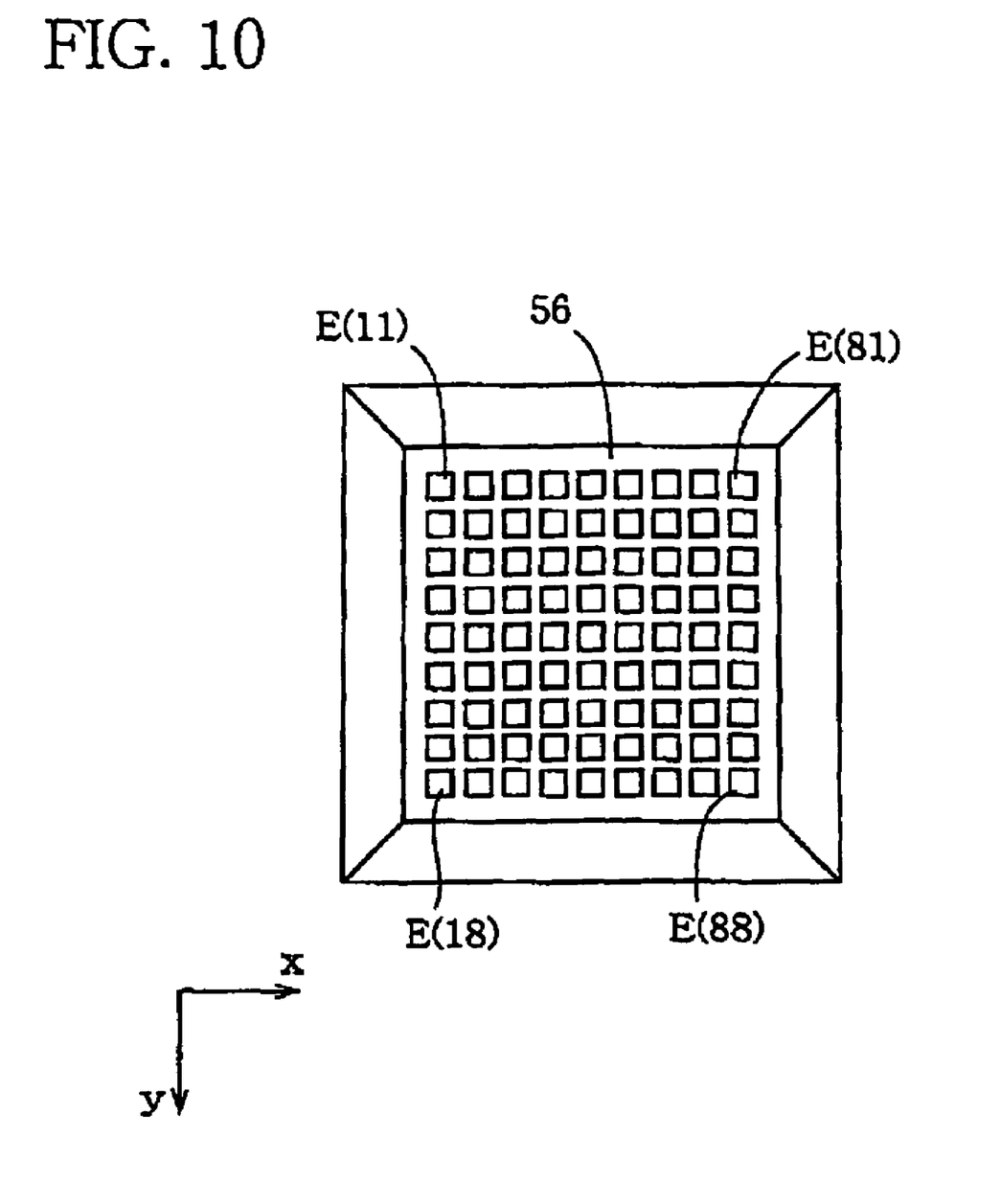
FIG. 10 is a plan view of a press surface of the pressure-pulse-wave detecting probe of FIG. 9.

Further, the probe 50 is different from the probe 10 of the above-described first embodiment, also in that the pressure detecting elements E are arranged in a plurality of rows on the press surface 56 of the sensor portion 54. More specifically described, a total of 64 pressure detecting elements E are two-dimensionally arranged in a lattice, as shown in FIG. 10. The 64 elements E are arranged on eight rows which are parallel with a X-axis direction and which are arranged in a Y-axis direction perpendicular to the X-axis direction. In other words, the 64 elements E are arranged on eight rows which are parallel with the Y-axis direction and which are arranged in the X-axis direction. In each of the eight rows parallel with the X-axis direction, eight elements E are arranged at a constant spacing interval. In each of the eight rows parallel with the Y-axis direction, eight elements E are arranged at a constant spacing interval. The 64 elements E thus arranged in the lattice cooperate with one another to have a square shape as a whole. In FIG. 10, each of the elements E are given two-digit number in the parenthesis, wherein the two-digit number represents the position of the element E in question as counted from the upper-left corner along the X-axis direction and the Y-axis direction.

Figure 11:
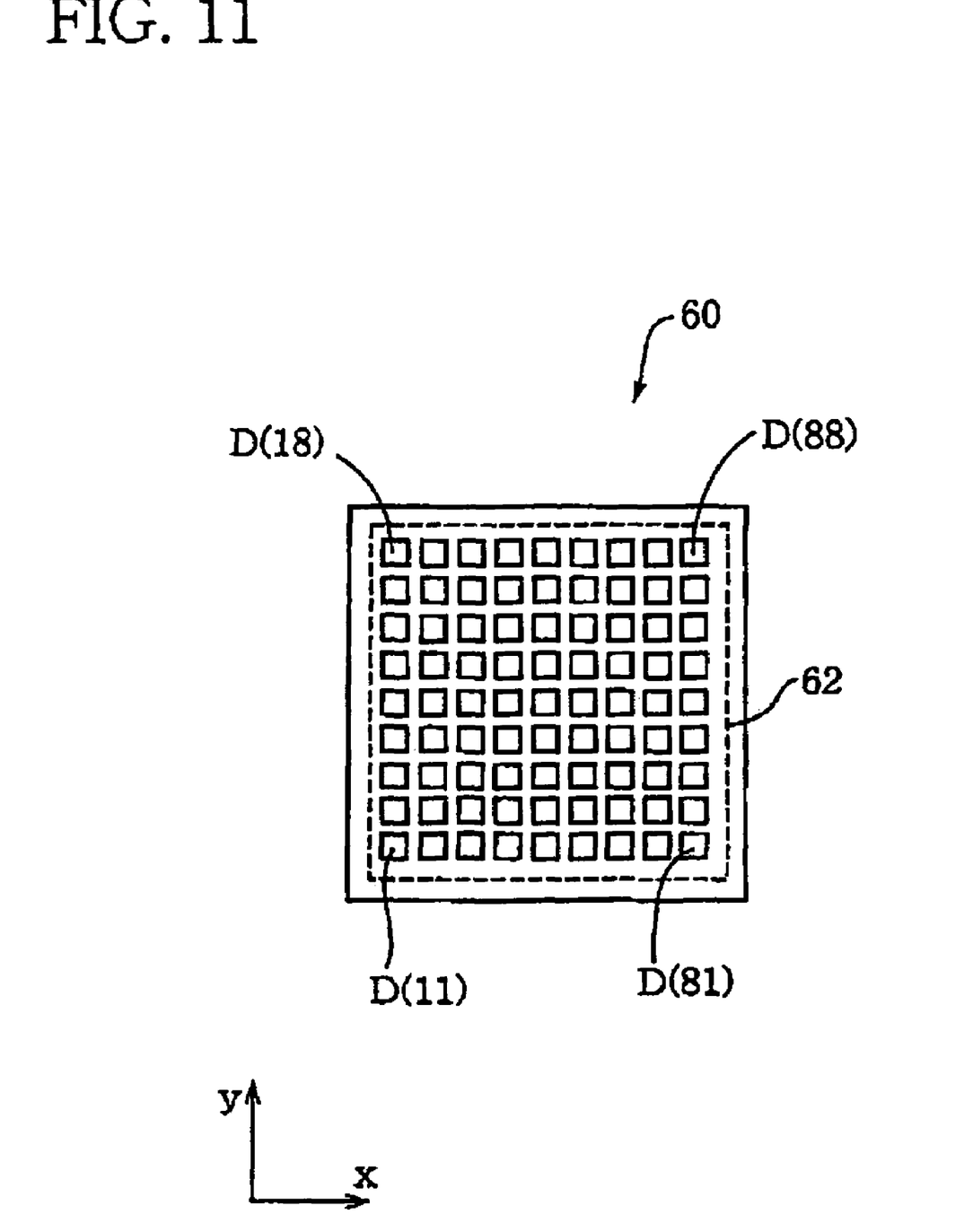
FIG. 11 is a view showing in enlargement an indicator provided in the pressure-pulse-wave detecting probe of FIG. 9.

FIG. 11 is a view showing in enlargement the indicator 60 having a plurality of indicating portions in the form of a total of 64 light emitters D which are positioned in respective positions corresponding to those of the pressure detecting elements E. The 64 light emitters D are two-dimensionally arranged in a lattice, and cooperate with one another to constitute a square-shaped indication face 62 That is, like the pressure detecting elements E, the light emitters D are arranged on eight rows which are parallel with the X-axis direction and which are arranged in the Y-axis direction, or arranged on eight rows which are parallel with the Y-axis direction and which are arranged in the X-axis direction.

Each of the light emitters D accommodates therein a plurality of light-emitting diodes (e.g., three light-emitting diodes) which are adapted to emit respective lights of different colors, so that each light emitter D is capable of emitting a light having a variable color. The color of light emitted by each light emitter D varies depending upon whether the pressure value detected by a corresponding one of the pressure detecting elements E (i.e., one of the elements E given the same number in the parenthesis as that of the light emitter D in question) is suitable for the detection of the pressure pulse wave or not. Where three light-emitting, diodes are accommodated in each light emitter D, or example, each light emitter D is capable of emitting a light having one of three colors, which one is selected depending upon whether the detected pressure value is equal to or higher than the minimum value of the optimum range, a little lower than the minimum value, or considerably lower than the minimum value. That is, one of the three light-emitting diodes accommodated in each light emitter D is selected on the basis of the pressure value detected by the corresponding pressure detecting element E, so as to be activated to emit the light. It is noted that each of the pressure detecting elements E and a corresponding one of the light emitters D (which indicates whether the pressure value detected by the pressure detecting element E in question is suitable for the detection of the pressure pulse wave or not) are positioned relative to each other, such that the position of each pressure detecting element in the press surface 56 corresponds to the position of the corresponding light emitter D in the indicator 60 as seen in a predetermined direction, or such that each pressure detecting element E is substantially aligned with the corresponding light emitter D in a longitudinal direction of the probe 50, as shown in FIG. 9.

Figure 12:
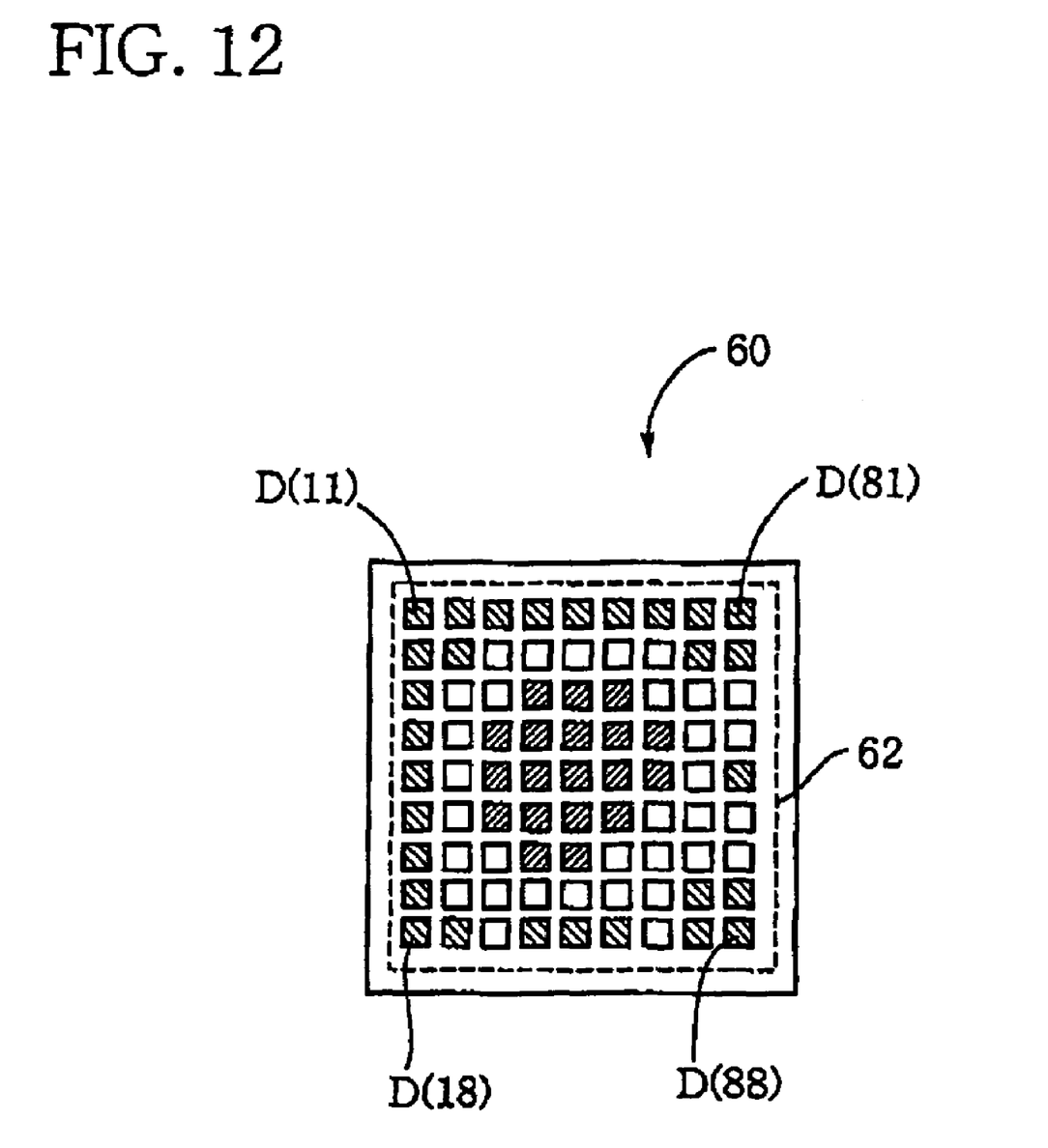
FIG. 12 is a view of an example of indication provided by the indicator of FIG. 11.

FIG. 12 is a view of an example of indication provided by the indicator 60. In the pressure-pulse-wave detecting probe 60 constructed according to the present embodiment of the invention, the indicator 60 is provided to be parallel with the press surface 56 of the sensor portion 54, namely, the plurality of light emitters D as the indicating portions are arranged on the plane parallel with the press surface 56 of the sensor, portion 54, such that the plural of light emitters D are positioned in the respective positions corresponding to those of the plurality of pressure detecting elements E. Each of the plurality of light emitters D is adapted to indicate whether the value of pressure detected by the corresponding one of the plurality of pressure detecting elements E is suitable for the detection of the pressure pulse wave or not, by changing the color of the light. This arrangement, in which the plurality of light emitters D are positioned in respective positions corresponding to those of the plurality of pressure detecting elements E, enables the operator who observes the indicator 60, to easily know a direction in which the probe 50 is to be displaced, when the position of the probe 50 has to be corrected While the presently preferred embodiments of this invention have been described in detail, or illustrative purpose only, it is to be understood that the present invention is not limited to the details of the illustrated embodiments, but may be otherwise embodied.

For example, in the first embodiment, whether the pressure value detected by each pressure detecting element E is suitable or the detection of the pressure pulse wave or not is represented by the color of the activated one or ones of the light-emitting diodes 24 of the corresponding indicating portion L, and the detected pressure value per se is represented by the length of the bar defined by the activated one or ones of the light-emitting diodes 24. However, in such a case where the pressure detecting elements E are arranged in a single row as in the first embodiment, only whether the detected pressure value is suitable for the detection of the pressure pulse wave or not may be represented by the change of the color of the activated light emitter, as in the second embodiment.

Further, in the above-described embodiments, the pressure value detected by each pressure detecting element E is continuously indicated by the indicator 22 or 60. However, in place of the detected pressure value, an amplitude (corresponding to a pulse pressure or a difference between maximum and minimum values in each pulse of the pressure signal supplied from each pressure detecting element E) of the pressure pulse wave detected by each pressure detecting element E may be continuously indicated by the indicator 22 or 60, in view of a fact that whether the pressure value is suitable for the detection of the pressure pulse wave or not can be determined not only on the basis of the pressure value detected by each pressure detecting element E but also on the basis of the amplitude of the pressure pulse wave detected by each pressure detecting element E. In this case, the pressure-pulse-wave detecting element includes a device or means for determining the amplitude of the pressure pulse wave on the basis of the pressure signal supplied from each pressure detecting element E, and such a device or means is provided, for example, in the arithmetic and control unit 38.

While the presently preferred embodiments of the present invention have been illustrated above, it is to be understood that the invention is not limited to the details of the illustrated embodiments, but may be embodied with various other changes, modifications and improvements, which may occur to those skilled in the art, without departing from the spirit and scope of the invention defined in the following claims.

What is claimed is:

1. A pressure-pulse-wave detecting probe for detecting a pressure pulse wave generated by an artery of a living subject, comprising:
    a sensor portion which has at least one pressure detecting element and a press surface that is to be positioned manually by an operator, relative to the artery of the subject, and is to be pressed manually by the operator, against the artery of the subject via a body surface of the subject, such that the pressure pulse wave is detected by said at least one pressure detecting element which is arranged on said press surface; and
    an indicator which is provided to be integral with said sensor portion, and provides an indication as to whether a value of pressure detected by each of said at least one pressure detecting element is suitable for detection of the pressure pulse wave or not;
    wherein said at least one pressure detecting element consists of a plurality of pressure detecting elements which are arranged in a row on said press surface,
    wherein said indicator has a plurality of indicating portions one of which indicates whether the value of pressure detected by one of said plurality of pressure detecting elements is suitable for the detection of the pressure pulse wave or not, and another of which indicates whether the value of pressure detected by another of said plurality of pressure detecting elements is suitable for the detection of the pressure pulse wave or not,
    and wherein said one of said plurality of indicating portions and said another of said plurality of indicating portions are arranged in a direction parallel with said row in which said plurality of pressure detecting elements are arranged.

2. A pressure-pulse-wave detecting probe according to claim 1,
    wherein each of said plurality of indication portions of said indicator has a plurality of light emitters each of which emits a light when activated,
    and wherein a number of activated ones of said plurality of light emitters of each of said plurality of indication portions is increased with an increase in the value of pressure detected by a corresponding one of said plurality of pressure detecting elements.

3. A pressure-pulse-wave detecting probe for detecting a pressure pulse wave generated by an artery of a living subject, comprising:
    a sensor portion which has at least one pressure detecting element and a press surface that is to be positioned manually by an operator, relative to the artery of the subject, and is to be pressed manually by the operator, against the artery of the subject via a body surface of the subject, such that the pressure pulse wave is detected by said at least one pressure detecting element which is arranged on said press surface; and
    an indicator which is provided to be integral with said sensor portion, and provides an indication as to whether a value of pressure detected by each of said at least one pressure detecting element is suitable for detection of the pressure pulse wave or not;
    wherein said at least one pressure detecting element consists of a plurality of pressure detecting elements which are arranged in a plurality of rows on said press surface,
    wherein said indicator has a plurality of indicating portions which are arranged on a plane parallel to said press surface such that said plurality of indicating portions are positioned in respective positions corresponding to those of said plurality of pressure detecting elements,
    and wherein each of said plurality of indicating portions indicates whether the value of pressure detected by a corresponding one of said plurality of pressure detecting elements is suitable for the detection of the pressure pulse wave or not.

4. A pressure-pulse-wave detecting probe according to claim 3, wherein each of said plurality of indicating portions emits a light having a color which varies depending upon whether the value of pressure detected by the corresponding one of said plurality of pressure detecting elements is suitable for the detection of the pressure pulse wave or not.

5. A pressure-pulse-wave detecting probe according to claim 3, wherein said plurality of pressure detecting elements are arranged in a lattice on said press surface, and said plurality of indicating portions are arranged in a lattice on said plane.

* * * * *